US009883816B2

(12) United States Patent
Inoue et al.

(10) Patent No.: US 9,883,816 B2
(45) Date of Patent: Feb. 6, 2018

(54) EYEWEAR

(71) Applicant: JIN CO., LTD., Gunma (JP)

(72) Inventors: Kazutaka Inoue, Tokyo (JP); Susumu Ichinohe, Saitama (JP); Jyunko Nakajima, Tokyo (JP)

(73) Assignee: JIN CO., LTD., Gunma (JP)

( * ) Notice: Subject to any disclaimer, the term of this patent is extended or adjusted under 35 U.S.C. 154(b) by 0 days.

(21) Appl. No.: 15/292,139

(22) Filed: Oct. 13, 2016

(65) Prior Publication Data

US 2017/0027470 A1    Feb. 2, 2017

Related U.S. Application Data

(63) Continuation of application No. PCT/JP2015/061383, filed on Apr. 13, 2015.

(30) Foreign Application Priority Data

Apr. 14, 2014  (JP) .................................. 2014-082796

(51) Int. Cl.
*A61B 5/0496* (2006.01)
*A61B 5/00* (2006.01)
(Continued)

(52) U.S. Cl.
CPC .............. *A61B 5/0496* (2013.01); *A61B 3/10* (2013.01); *A61B 5/683* (2013.01); *A61B 5/6803* (2013.01); *A61B 5/6814* (2013.01); *A61B 5/6821* (2013.01); *G02C 5/12* (2013.01); *G02C 11/00* (2013.01); *G02C 11/10* (2013.01); *A61B 3/113* (2013.01)

(58) Field of Classification Search
CPC ... A61B 5/0478; A61B 5/0496; A61B 5/0531; A61B 5/6803; A61B 5/6814; A61B 5/6821; A61B 5/683
See application file for complete search history.

(56) References Cited

U.S. PATENT DOCUMENTS 4,331,163 A    5/1982  Nomura
5,495,853 A *  3/1996  Yasushi ................ A61B 5/0482
                                                        600/27
(Continued)

FOREIGN PATENT DOCUMENTS

JP    H5-508562 A    12/1993

OTHER PUBLICATIONS

International Preliminary Report on Patentability for International Application No. PCT/JP2015/061383 issued by the International Bureau of WIPO dated Oct. 27, 2016.
(Continued)

*Primary Examiner* — Lee S Cohen

(57) ABSTRACT

A technique to detect an eye potential of a wearer of an eyewear by using an electrode abutting on the glabella of the wearer has been known, but it is desirable to surely cause the electrode to abut on the glabella so as to prevent deterioration in the detection accuracy of detecting a biosignal indicating an eye potential, myogenic potential, brain wave or the like. In view of this, an eyewear including: a frame; a first electrode that abuts on a glabella of a wearer of the eyewear; and an electrode holding unit that holds the first electrode such that a distance between the frame and the first electrode is changeable is included.

7 Claims, 6 Drawing Sheets

(51) Int. Cl.
 *A61B 3/10* (2006.01)
 *G02C 11/00* (2006.01)
 *G02C 5/12* (2006.01)
 *A61B 3/113* (2006.01)

(56) References Cited

U.S. PATENT DOCUMENTS

| | | |
|---|---|---|
| 9,398,864 B2 * | 7/2016 | Lawrence |
| 9,433,774 B2 * | 9/2016 | Dar ..................... A61B 5/0478 |
| 2004/0070729 A1 | 4/2004 | Wiebe et al. |
| 2007/0276451 A1 * | 11/2007 | Rigaux ................ A61N 1/0452 607/48 |
| 2013/0184782 A1 | 7/2013 | Eipper et al. |
| 2013/0324881 A1 * | 12/2013 | Kanoh ..................... A61B 3/10 600/547 |
| 2014/0228652 A1 * | 8/2014 | Terada ................ A61B 5/0478 600/301 |

OTHER PUBLICATIONS

International Search Report for International Application No. PCT/JP2015/081383, issued by the Japan Patent Office dated Jun. 23, 2015.

Extended European Search Report for European Patent Application No. 15780095.4, issued by the European Patent Office dated Apr. 6, 2017.

* cited by examiner

EYEWEAR

The contents of the following patent applications are incorporated herein by reference: No. JP2014-082796 filed in JP on Apr. 14, 2014 and PCT/JP2015/061383 filed on Apr. 13, 2015.

BACKGROUND

1. Technical Field

The present invention relates to an eyewear.

2. Related Art

A technique to detect an eye potential of a wearer of an eyewear by using an electrode abutting on the glabella of the wearer has been known (please see Patent Document 1, for example).

PRIOR ART TECHNICAL DOCUMENTS

Patent Documents

[Patent Document 1] Japanese Patent Application Publication No. 2013-244370

It is desirable to surely cause the electrode to abut on the glabella so as to prevent deterioration in the detection accuracy of detecting a biosignal indicating an eye potential or the like.

DESCRIPTION OF EXEMPLARY EMBODIMENTS

Hereinafter, (some) embodiment(s) of the present invention will be described. The embodiment(s) do(es) not limit the invention according to the claims, and all the combinations of the features described in the embodiment(s) are not necessarily essential to means provided by aspects of the invention.

Figure 1:
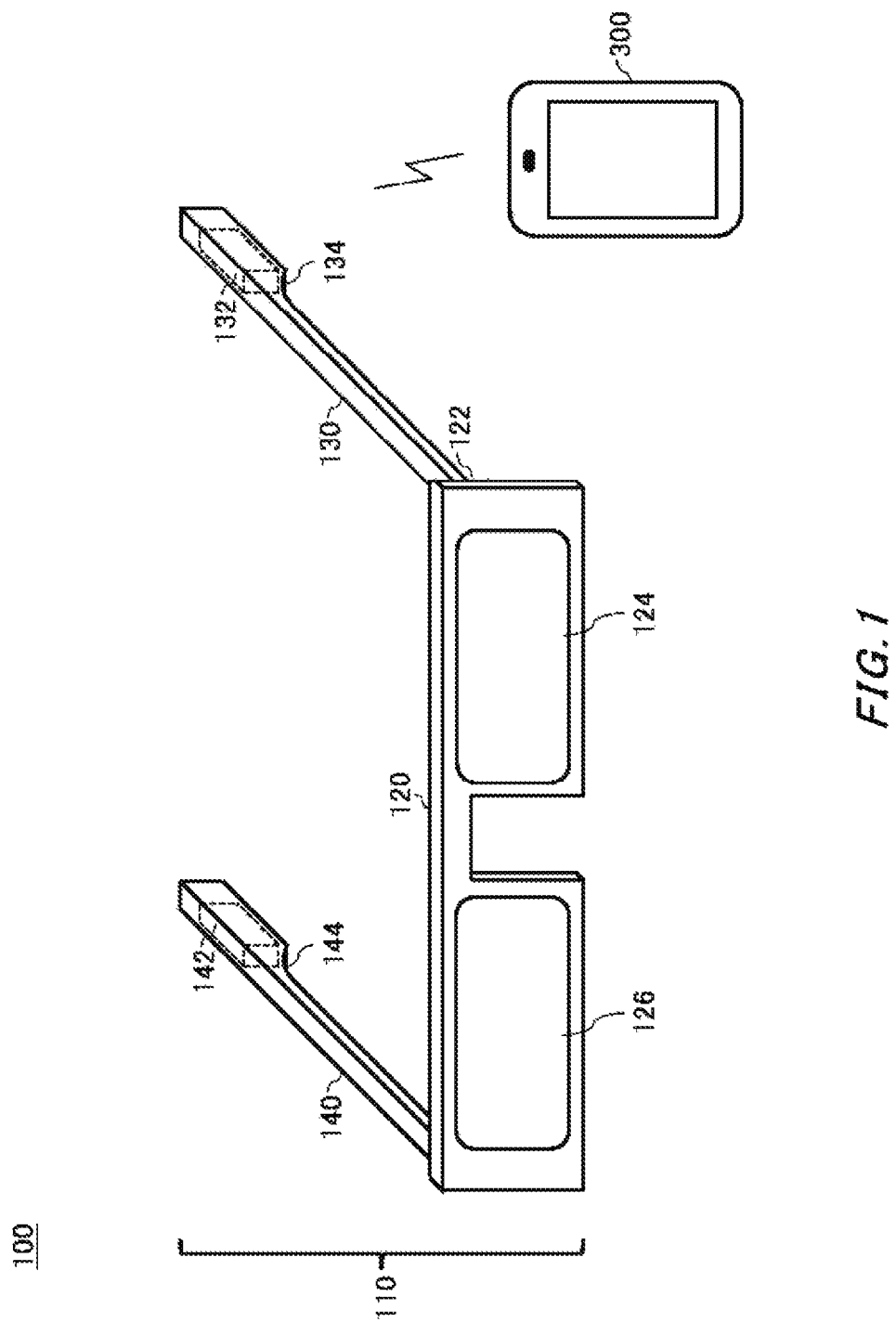
FIG. 1 schematically illustrates one example of eyeglasses.
Figure 2:
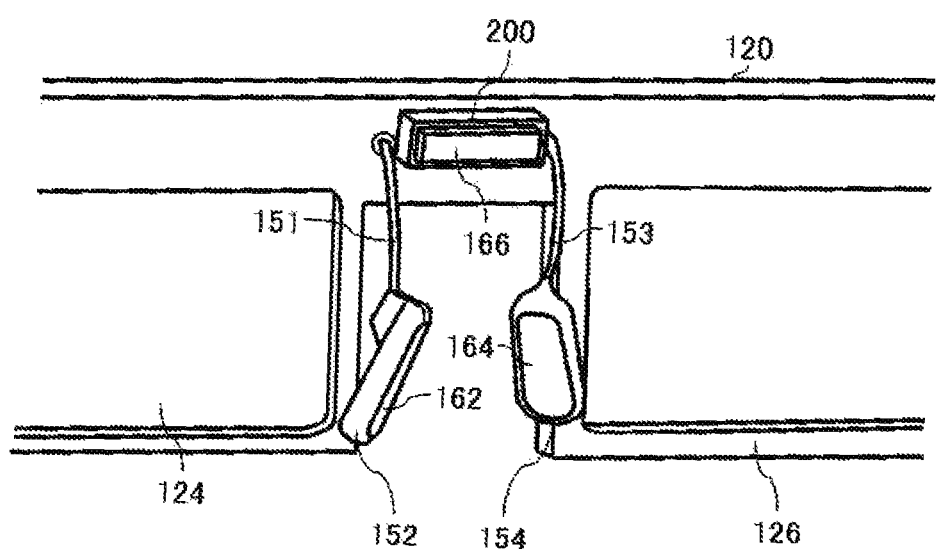
FIG. 2 schematically illustrates one example of eyeglasses.

FIG. 1 and FIG. 2 schematically illustrate one example of eyeglasses 100. FIG. 1 is a perspective view of the eyeglasses 100. FIG. 2 is a partially enlarged view of the eyeglasses 100 seen from behind. The eyeglasses 100 may be one example of an eyewear.

The eyeglasses 100 according to the present embodiment includes a frame 110, a left lens 124 and a right lens 126. The frame 110 has a front 120, a left temple 130 and a right temple 140.

The front 120 has: a rim 122 that holds the left lens 124 and the right lens 126; a left nose pad 152; a right nose pad 154 and a glabella electrode unit 200.

The left nose pad 152 is supported by a support member 151 placed in the front 120. The support member 151 may be a linear member having one end that is placed in the front 120, and another end that supports the left nose pad 152. A left electrode 162 is placed on a front surface of the left nose pad 152. The left electrode 162 abuts on the nose of a wearer 10 when the wearer 10 who is to wear the eyeglasses 100 wears the eyeglasses 100.

The right nose pad 154 is supported by a support member 153 placed in the front 120. The support member 153 may be a linear member having one end that is placed in the front 120, and another end that supports the right nose pad 154. A right electrode 164 is placed on a front surface of the right nose pad 154. The right electrode 164 abuts on the nose of the wearer 10 when the wearer 10 wears the eyeglasses 100.

The glabella electrode unit 200 may be arranged to be positioned in front of the glabella of the wearer 10 when the wearer 10 wears the eyeglasses 100. A glabella electrode 166 is placed on a front surface of the glabella electrode unit 200. The glabella electrode 166 abuts on the glabella of the wearer 10 when the wearer 10 wears the eyeglasses 100. The glabella electrode unit 200 may be arranged at any position of the frame 110 as long as such a position can cause the glabella electrode 166 to abut on the glabella of the wearer 10. The glabella electrode unit 200 is placed for example in the bridge of the frame 110. The glabella electrode 166 may be one example of a first electrode.

The left temple 130 has a circuit board 132 and an earth electrode 134. The earth electrode 134 is electrically connected to the circuit board 132. The earth electrode 134 may be arranged on a lower surface of the left temple 130. The earth electrode 134 may be arranged at a position at which it abuts on an upper portion of an ear of the wearer 10 when the wearer 10 wears the eyeglasses 100.

The right temple 140 has a battery 142 and a reference electrode 144. The battery 142 is electrically connected to the circuit board 132 via the right temple 140, the front 120 and the left temple 130. A wire that electrically connects the battery 142 and the circuit board 132 is for example embedded in the frame 110. The battery 142 supplies electrical power to the circuit board 132.

The reference electrode 144 may be arranged on a lower surface of the right temple 140. The reference electrode 144 may be arranged at a position at which it abuts on an upper portion of an ear of the wearer 10 when the wearer 10 wears the eyeglasses 100. The reference electrode 144 is electrically connected to the circuit board 132 via the right temple 140, the front 120 and the left temple 130. A wire that electrically connects the reference electrode 144 and the circuit board 132 is for example embedded in the frame 110.

The left electrode 162 is electrically connected with the circuit board 132 via the left nose pad 152, the support member 151, the front 120 and the left temple 130. A wire that electrically connects the left electrode 162 and the circuit board 132 is for example embedded in the left nose pad 152, the support member 151, the front 120 and the left temple 130.

The right electrode 164 is electrically connected with the circuit board 132 via the right nose pad 154, the support member 153, the front 120 and the left temple 130. A wire that electrically connects the right electrode 164 and the circuit board 132 is for example embedded in the right nose pad 154, the support member 153, the front 120 and the left temple 130. The left electrode 162 and the right electrode 164 may be one example of a pair of second electrodes.

The glabella electrode 166 is electrically connected with the circuit board 132 via the glabella electrode unit 200, the front 120 and the left temple 130. The glabella electrode 166 is electrically connected with the glabella electrode unit 200. A wire that electrically connects the glabella electrode unit 200 and the circuit board 132 may be embedded in the front 120 and the left temple 130.

The circuit board 132 according to the present embodiment may detect an eye potential by using the left electrode 162, the right electrode 164, the glabella electrode 166, the earth electrode 134 and the reference electrode 144. The circuit board 132 may be one example of an eye potential detecting unit. The circuit board 132 may process a detected eye potential. The circuit board 132 may process an eye potential by using electrical power supplied from the battery 142.

Processing an eye potential may be performing arithmetic processing on the eye potential. For example, the circuit board 132 performs adding and subtracting processing on an eye potential of the left electrode 162 relative to the glabella electrode 166 as its reference, and an eye potential of the right electrode 164 relative to the glabella electrode 166 as its reference. Also, processing an eye potential may be performing signal amplification processing on the eye potential. Also, processing an eye potential may be performing digitization processing on an eye potential signal.

Also, processing an eye potential may be transmitting the eye potential. For example, the circuit board 132 transmits an eye potential to an information terminal 300. The circuit board 132 may transmit an eye potential to the information terminal 300 by wireless communication. For example, the circuit board 132 transmits an eye potential to the information terminal 300 by using a wireless LAN such as Bluetooth (registered trademark), Wi-Fi (registered trademark) or the like. The information terminal 300 may be a mobile phone such as a smartphone, a tablet terminal, PC (Personal Computer) or the like.

Also, processing an eye potential may be, according to the eye potential, detecting a line of sight of a wearer of the eyeglasses 100, detecting a blink, detecting sleepiness, or the like. The circuit board 132 may transmit, to the information terminal 300, a detection result about a line of sight, a detection result about his/her blink, a detection result about his/her sleepiness, or the like.

Figure 3:
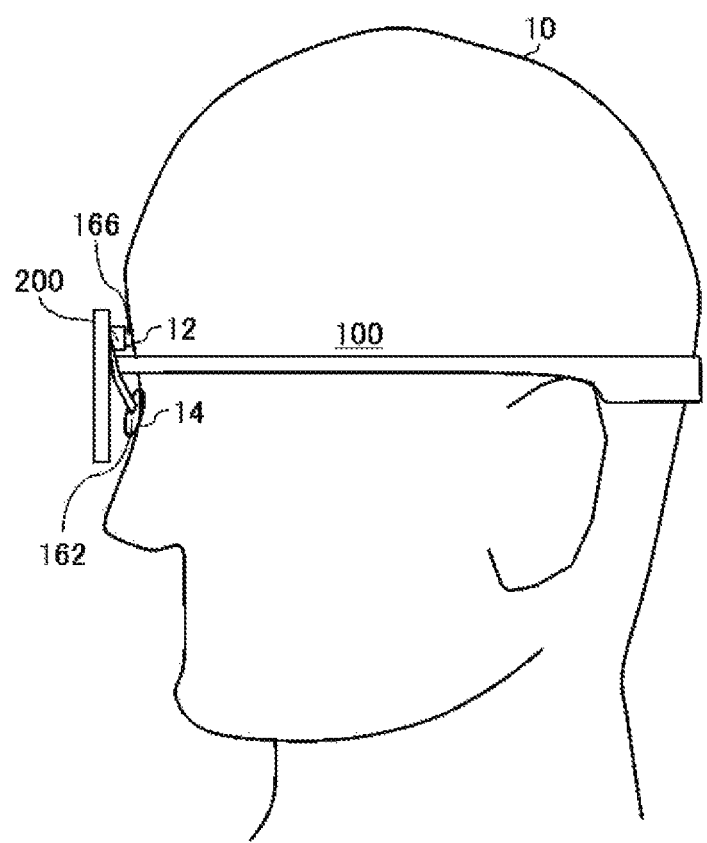
FIG. 3 schematically illustrates a state where a wearer wears eyeglasses.

FIG. 3 schematically illustrates a state where the wearer 10 wears the eyeglasses 100. As illustrated in FIG. 3, the glabella electrode 166 abuts on the glabella 12 of the wearer 10. Also, the left electrode 162 abuts on a nose 14 of the wearer 10. Similarly, the right electrode 164 also abuts on the nose 14 of the wearer 10.

The left electrode 162, the right electrode 164 and the glabella electrode 166 desirably always keep surely abutting on the wearer 10 so as to continuously detect an eye potential of the wearer 10 while the wearer 10 wears the eyeglasses 100. Also, when an impact is applied to the eyeglasses 100, desirably the glabella electrode 166 is pushed onto the glabella 12 of the wearer 10, and thereby application of an excessive impact to the glabella 12 can be prevented.

In view of this, the glabella electrode unit 200 according to the the present embodiment holds the glabella electrode 166 such that a distance between the frame 110 and the glabella electrode 166 is changeable. The glabella electrode unit 200 may be one example of an electrode holding unit.

Figure 4:
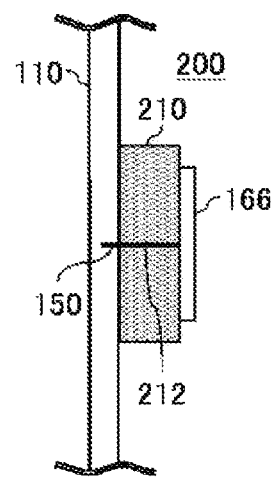
FIG. 4 schematically illustrates one example of a glabella electrode unit.

FIG. 4 schematically illustrates one example of the glabella electrode unit 200. The glabella electrode unit 200 may have an elastic member 210 and a wire 212. The elastic member 210 is placed in the frame 110, and holds the glabella electrode 166. The wire 212 electrically connects the glabella electrode 166, and a wire 150 embedded in the frame 110. The wire 150 electrically connects the wire 212 and the circuit board 132.

By the elastic member 210 holding the glabella electrode 166, the distance between the frame 110 and the glabella electrode 166 can be made changeable. For example, if the wearer 10 wears the eyeglasses 100 and the glabella electrode 166 is pushed onto the elastic member 210, the distance between the frame 110 and the glabella electrode 166 becomes short. In this manner, by the elastic member 210 holding the glabella electrode 166, even if relative positions of the wearer 10 and the eyeglasses 100 change, the elastic force of the elastic member 210 allows the glabella electrode 166 and the glabella 12 to remain abutting on each other. Also, if the glabella electrode units 200 are to be placed in respective ones among a plurality of pairs of eyeglasses worn by a plurality of the wearers 10, by the glabella electrode units 200 making changeable the distances between the frames 110 and the glabella electrodes 166, differences in distances between the glabellas 12 of the wearers 10 and the frames 110 can be absorbed for each wearer 10 among the plurality of wearers 10 and for each pair of eyeglasses among the plurality of pairs of eyeglasses. Also, if an impact is applied to the eyeglasses 100, the impact can be absorbed by the elastic member 210, and an impact to be applied to the glabella 12 can be reduced.

The elastic member 210 may be any member as long as it has elasticity. For example, the elastic member 210 is elastomer resin.

Figure 5:
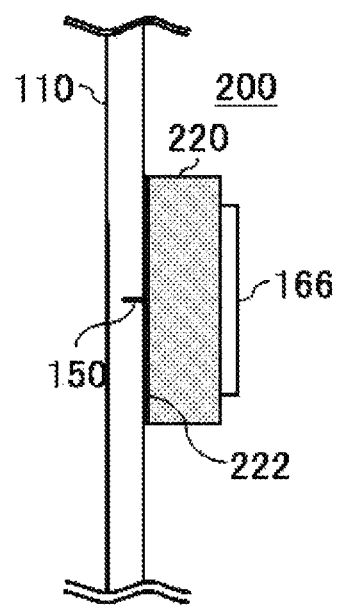
FIG. 5 schematically illustrates another example of the glabella electrode unit.

FIG. 5 schematically illustrates another example of the glabella electrode unit 200. The glabella electrode unit 200 may have a conductive member 220 and a wire joining unit 222. The conductive member 220 and the wire joining unit 222 are placed in the frame 110. The conductive member 220 has elasticity and conductivity. The conductive member 220 holds the glabella electrode 166.
The wire joining unit 222 electrically connects the conductive member 220 and the wire 150.

By the conductive member 220 holding the glabella electrode 166, the distance between the frame 110 and the glabella electrode 166 can be made changeable. For example, if the wearer 10 wears the eyeglasses 100 and the glabella electrode 166 is pushed onto the conductive member 220, the distance between the frame 110 and the glabella electrode 166 becomes short. In this manner, by the conductive member 220 holding the glabella electrode 166, even if relative positions of the wearer 10 and the eyeglasses 100 change, the elastic force of the conductive member 220 allows the glabella electrode 166 and the glabella 12 to remain abutting on each other. Also, if an impact is applied to the eyeglasses 100, the impact can be absorbed by the conductive member 220, and an impact to be applied to the glabella 12 can be reduced.

The conductive member 220 may be any member as long as it has elasticity and conductivity. For example, the conductive member 220 is conductive sponge. Also, the conductive member 220 may be conductive rubber. Also, the conductive member 220 may be conductive resin having elasticity.

Figure 6:
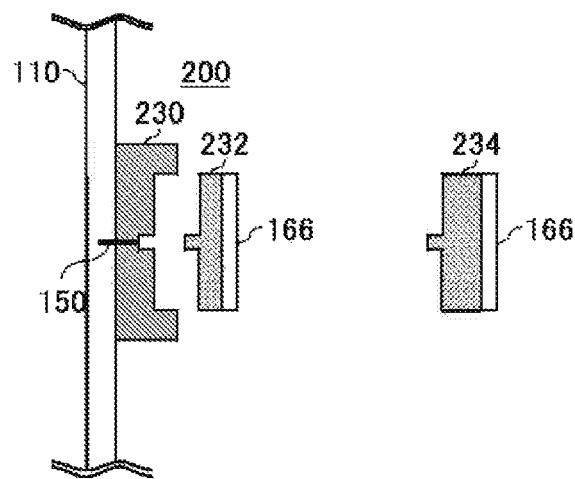
FIG. 6 schematically illustrates another example of the glabella electrode unit.

FIG. 6 schematically illustrates another example of the glabella electrode unit 200. The glabella electrode unit 200 may have a connector 230 and a connector 232. The connector 230 is placed in the frame 110. The connector 232 holds the glabella electrode 166. The glabella electrode 166 may be provided on a front surface of the connector 232.

The connector 232 is attachable to and detachable from the connector 230, and electrically connects the glabella electrode 166 to the connector 230. The connector 230 electrically connects the glabella electrode 166 and the wire 150. The connector 230 may be one example of a first connector. The connector 232 may be one example of a second connector.

A connector 234 with a height which is different from the height of the connector 232 may be coupled to the connector 230. The connector 234 may be one example of a second connector. Due to the connector 232 and the connector 234 with different heights being attachable to and detachable from the connector 230, the distance between the frame 110 and the glabella electrode 166 can be made changeable.

The connector 230 and at least either of the connector 232 and the connector 234 may have elasticity. Thereby, if an impact is applied to the eyeglasses 100, the impact can be absorbed by the connector 230 and at least either of the connector 232 and the connector 234, and an impact to be applied to the glabella 12 can be reduced.

Figure 7:
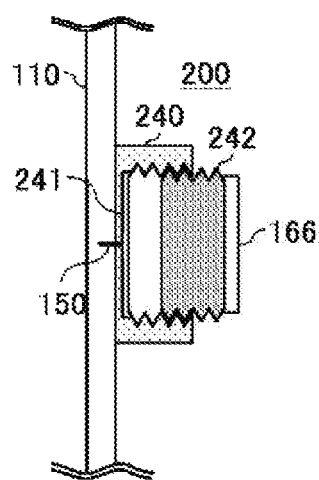
FIG. 7 schematically illustrates another example of the glabella electrode unit.

FIG. 7 schematically illustrates another example of the glabella electrode unit 200. The glabella electrode unit 200 may have a first member 240 and a second member 242. The first member 240 is placed in the frame 110. The second member 242 holds the glabella electrode 166. The glabella electrode 166 may be provided on a front surface of the second member 242.

The first member 240 holds the second member 242. The first member 240 and the second member 242 may be electrically connected at a contact portion between the first member 240 and the second member 242. The first member 240 may have a wire 241, and the second member 242 and the wire 150 may be electrically connected by the wire 241. The second member 242 and the glabella electrode 166 may be electrically connected. The glabella electrode 166 may be electrically connected to the wire 150 via the contact portion between the first member 240 and the second member 242, and the wire 241.

The second member 242 moves relative to the first member 240. For example, the first member 240 holds the second member 242 by a screw structure. Thereby, by rotating the second member 242, the distance between the frame 110 and the glabella electrode 166 can be changed.

Also, the first member 240 may hold the second member 242 such that if a certain degree (or higher degrees) of force is applied thereto, the distance between the frame 110 and the glabella electrode 166 changes stepwise. For example, it has a structure in which the first member 240 locks the second member 242 with a plurality of steps, and if a certain degree (or higher degrees) of force is applied, the lock is unlocked. Thereby, the distance between the frame 110 and the glabella electrode 166 can be changed. Also, if an impact is applied to the eyeglasses 100, the second member 242 moves stepwise relative to the first member 240, and so the impact can be absorbed.

The connector 230 and at least either of the connector 232 and the connector 234 may have elasticity. Thereby, if an impact is applied to the eyeglasses 100, the impact can be absorbed by the connector 230 and at least either of the connector 232 and the connector 234, and an impact to be applied to the glabella 12 can be reduced.

The explanation in relation to FIG. 7 is about an example in which the first member 240 contains the second member 242, but this is not the only example. The second member 242 may contain the first member 240.

Figure 8:
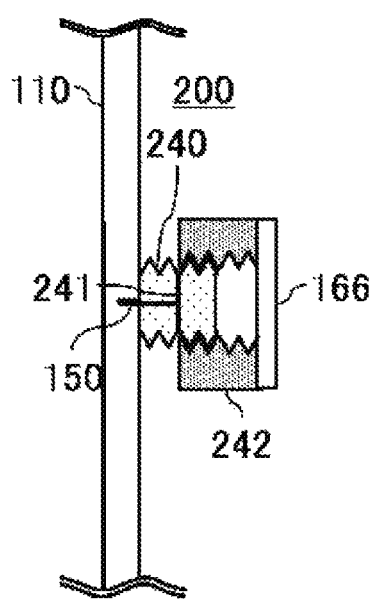
FIG. 8 schematically illustrates another example of the glabella electrode unit.

FIG. 8 schematically illustrates another example of the glabella electrode unit 200. FIG. 8 exemplarily illustrates an example in which the second member 242 contains the first member 240.

The explanation in the present embodiment is about an example in which the left temple 130 has the earth electrode 134, and the right temple 140 has the reference electrode 144, but the left temple 130 may have the reference electrode 144, and the right temple 140 may have the earth electrode 134. Also, the explanation in the present embodiment is about an example in which the left temple 130 has the circuit board 132, and the right temple 140 has the battery 142, but the left temple 130 may have the battery 142, and the right temple 140 may have the circuit board 132.

Also, in the present embodiment, the eyeglasses 100 that detect an eye potential is explained as one example of an eyewear, but this is not the only example. The eyewear may be any eyeglasses as long as they use an electrode. For example, the eyewear is eyeglasses that processes a brain wave, eyeglasses that processes images, eyeglasses that processes sound, or the like.

Also, in the present embodiment, the eyeglasses 100 is explained as an example of an eyewear, but this is not the only example. The eyewear may be sunglasses, a head mount display, or the like.

The shape of each part of the eyeglasses 100 illustrated in FIG. 1 to FIG. 3 is exemplary, and the shape is not limited to the one illustrated in the figures.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

EXPLANATION OF REFERENCE SYMBOLS

10: wearer; 12: glabella; 14: nose; 100: eyeglasses; 110: frame; 120: front; 122: rim; 124: left lens; 126: right lens; 130: left temple; 132: circuit board; 134: earth electrode; 140: right temple; 142: battery; 144: reference electrode; 150: wire; 151: support member; 152: left nose pad; 153: support member; 154: right nose pad; 162: left electrode; 164: right electrode; 166: glabella electrode; 200: glabella electrode unit; 210: elastic member; 212: wire; 220: conductive member; 222: wire joining unit; 230: connector; 232: connector; 234: connector; 240: first member; 241: wire; 242: second member; 300: information terminal

What is claimed is:
1. An eyewear set comprising:
a frame;

a first electrode positioned to abut on a glabella of a wearer of the eyewear; and an electrode holding unit that holds the first electrode such that a distance between the frame and the first electrode is changeable, wherein the electrode holding unit has:
- a first connector placed in the frame,
- a second connector that is attachable to and detachable from the first connector, and electrically connects the first electrode to the first connector, and
- a third connector that is attachable to and detachable from the first connector, and electrically connects the first electrode to the first connector, the third connector having a height different from that of the second connector;

wherein the first connector is configured to interchangeably connect to the second connector and the third connector, the first electrode is provided on a front surface of the second connector or a front surface of the third connector, and the distance between the frame and the first electrode is defined as a total length of a thickness of the first connector and a thickness of the second connector, or a total length of a thickness of the first connector and a thickness of the third connector.

2. The eyewear set according to claim 1, wherein the electrode holding unit includes an elastic member.

3. The eyewear set according to claim 2, wherein the elastic member includes a conductive member electrically connected with the first electrode.

4. The eyewear set according to claim 3, wherein the elastic member is conductive sponge, conductive rubber or conductive resin.

5. The eyewear set according to claim 1, further comprising:
- a pair of nose pads connected to the frame; and
- a pair of second electrodes placed on front surfaces of the pair of nose pads.

6. The eyewear set according to claim 5, further comprising an eye potential detecting unit that is electrically connected to the first electrode and the pair of second electrodes, and detects an eye potential of the wearer.

7. The eyewear set according to claim 1, wherein at least one of the first connector, the second connector and the third connector includes an elastic member formed of conductive material.

* * * * *